(12) United States Patent
Salstrom et al.

(10) Patent No.: US 9,144,665 B2
(45) Date of Patent: Sep. 29, 2015

(54) FLEXIBLE SHEATH ASSEMBLIES AND INTERVENTIONAL CATHETER SYSTEMS INCORPORATING THEM

(75) Inventors: Jared Salstrom, Renton, WA (US);
Casey Torrance, Snohomish, WA (US);
William Kanz, Woodinville, WA (US)

(73) Assignee: Boston Scientific Limited, Hamilton (BM)

( * ) Notice: Subject to any disclaimer, the term of this patent is extended or adjusted under 35 U.S.C. 154(b) by 1071 days.

(21) Appl. No.: 13/206,432

(22) Filed: Aug. 9, 2011

(65) Prior Publication Data

US 2015/0231367 A1    Aug. 20, 2015

Related U.S. Application Data

(60) Provisional application No. 61/401,289, filed on Aug. 9, 2010.

(51) Int. Cl.
*A61M 25/00* (2006.01)
*A61M 25/01* (2006.01)

(52) U.S. Cl.
CPC ....... *A61M 25/0138* (2013.01); *A61M 25/0054* (2013.01); *A61M 25/0113* (2013.01); *A61M 25/0147* (2013.01)

(58) Field of Classification Search
CPC ................ A61M 25/0097; A61M 2025/0161; A61M 25/0053; A61M 25/00; A61M 2025/0004; A61M 25/0012; A61M 25/0013; A61M 25/0014; A61M 25/0043; A61M 25/005; A61M 25/0051; A61M 25/0052; A61M 25/0054; A61M 25/0045
USPC .......................................................... 604/525
See application file for complete search history.

(56) References Cited

U.S. PATENT DOCUMENTS

| | | | |
|---|---|---|---|
| 4,547,193 | A | 10/1985 | Rydell |
| 4,917,088 | A | 4/1990 | Crittenden |
| 4,960,410 | A | 10/1990 | Pinchuk |
| 5,573,520 | A | 11/1996 | Schwartz et al. |
| 5,599,326 | A | 2/1997 | Carter |
| 5,741,429 | A | 4/1998 | Donadio, III et al. |
| 5,769,828 | A | 6/1998 | Jonkman |
| 5,843,050 | A | 12/1998 | Jones et al. |
| 5,961,510 | A | 10/1999 | Fugoso et al. |
| 6,102,890 | A | 8/2000 | Stivland et al. |
| 6,107,004 | A | 8/2000 | Donadio, III |
| 7,294,124 | B2 | 11/2007 | Eidenschink |
| 7,878,984 | B2 | 2/2011 | Jacobsen et al. |
| 7,879,022 | B2 | 2/2011 | Bonnette et al. |
| 2005/0059957 | A1 | 3/2005 | Campbell et al. |
| 2006/0100687 | A1 | 5/2006 | Fahey et al. |

(Continued)

FOREIGN PATENT DOCUMENTS

| | | |
|---|---|---|
| EP | 0437795 B1 | 10/1997 |
| EP | 1 382 366 A1 | 1/2004 |

*Primary Examiner* — Jason Flick
(74) *Attorney, Agent, or Firm* — Seager, Tufte & Wickhem LLP

(57) ABSTRACT

Sheath assemblies incorporating slotted structures at one or more areas provide areas of different flexibility and bendability characteristics along the length of the sheath assembly. An inner tubular member has an arrangement of discontinuous slots along at least a portion of its length, with at least some of the slots terminating in an enlarged aperture at at least one terminus of the slot, and a flexible outer tubular member contacts and extends over at least a portion of the inner tubular member.

18 Claims, 4 Drawing Sheets

(56) References Cited

U.S. PATENT DOCUMENTS

| | | |
|---|---|---|
| 2006/0241564 A1 | 10/2006 | Corcoran et al. |
| 2008/0097398 A1* | 4/2008 | Mitelberg et al. ............. 604/525 |
| 2009/0062602 A1 | 3/2009 | Rosenberg et al. |
| 2009/0157162 A1* | 6/2009 | Chow et al. .................. 623/1.11 |

\* cited by examiner

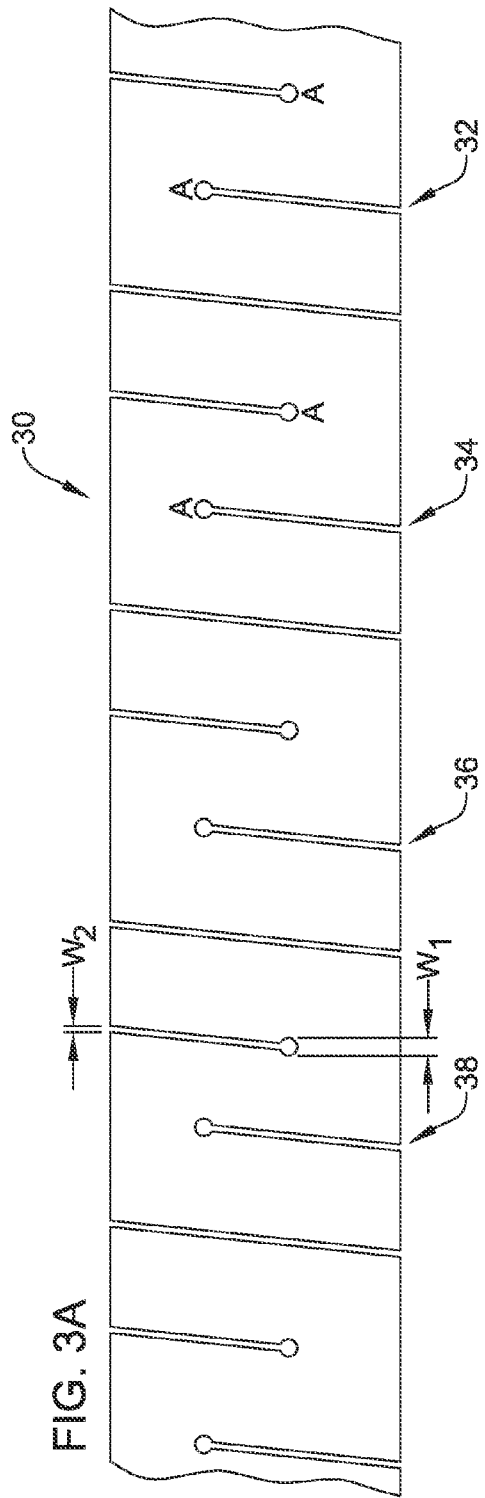
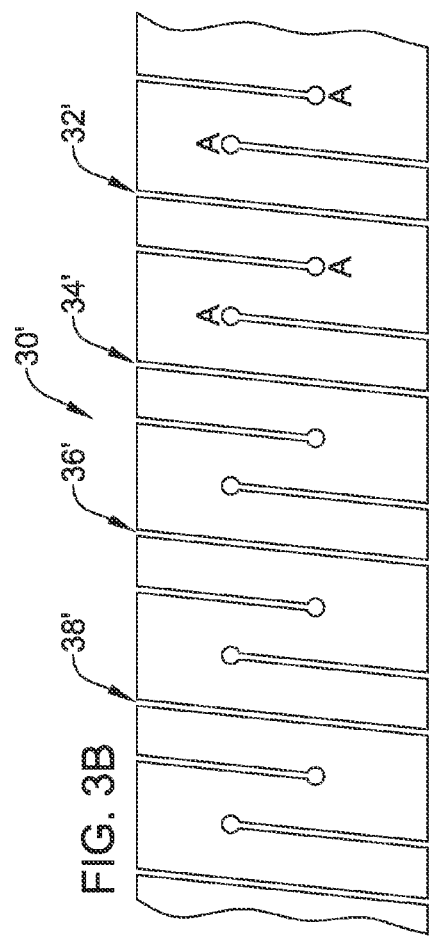

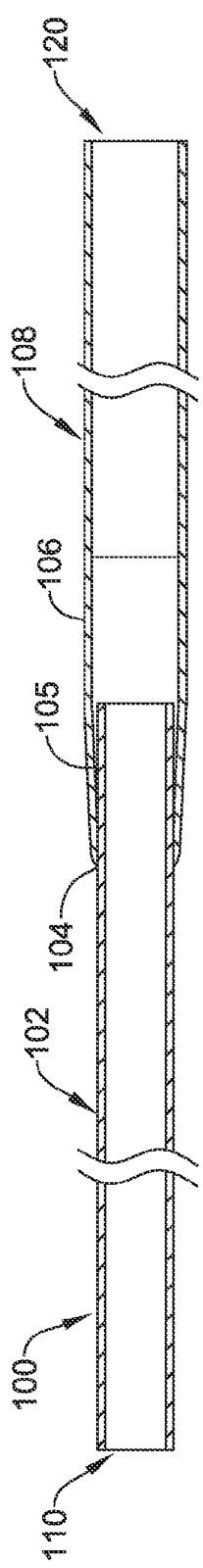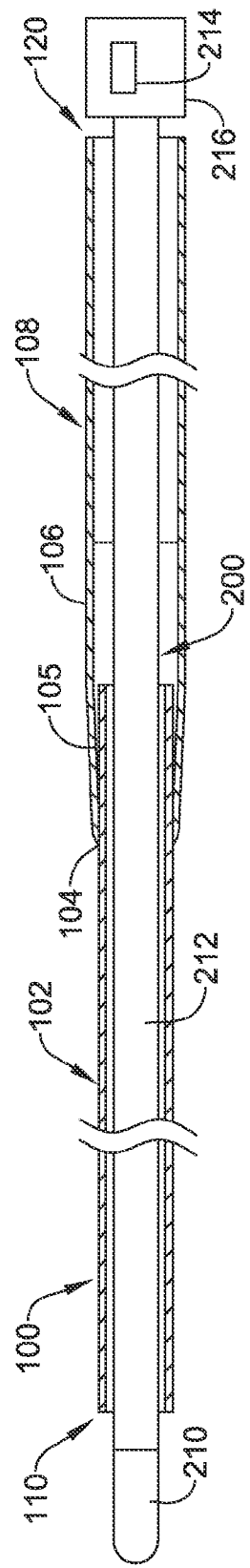

FLEXIBLE SHEATH ASSEMBLIES AND INTERVENTIONAL CATHETER SYSTEMS INCORPORATING THEM

REFERENCE TO RELATED APPLICATION

This application claims priority to U.S. Provisional Patent Application No. 61/401,289 filed Aug. 9, 2010. The disclosure of the priority application is incorporated by reference herein in its entirety.

FIELD OF THE INVENTION

The present invention relates, generally, to flexible structures, such as flexible sheath assemblies, for use in medical devices such as interventional catheter systems. More particularly, the present invention relates to flexible sheath assemblies, and flexible sheath assemblies incorporated in interventional catheter systems having aspiration and/or infusion systems. Flexible sheath assemblies are also useful in other types of flexible tubing applications and medical devices.

BACKGROUND OF THE INVENTION

Catheters are flexible tubes used for navigating internal body vessels and lumens and guiding devices within the body, such as in the vasculature, urinary tract, spinal column, fallopian tubes, bile ducts, and the like, and are often used in connection with minimally invasive diagnostic or surgical techniques. Catheters may be used for medical procedures to examine, diagnose and treat internal conditions while positioned at a target location within the body that is otherwise inaccessible. An intravascular catheter, for example, is generally inserted and advanced through a valved introducer fitting into a blood vessel near the surface of the body, such as the femoral artery, and is guided through the vasculature to a desired location. Catheters are used for coronary vascular and cardiac-related interventional operations, as well as neurovascular interventions, peripheral vascular, renal, and other types of intravascular interventions. Medical devices and instruments may be guided, through the catheter, to the desired site and operated.

Catheters must generally be flexible enough to readily navigate a tortuous path, such as a path through tortuous vasculature, without getting stuck at tight turns, and without damaging tissue. Catheters must also be stiff enough to provide "pushability" along a path, such as through the vasculature. When catheters are used as a conduit for various tools, interventional devices, fluids, and the like, they provide support for internally guided tools, devices, fluids, etc., and they and must maintain a generally consistent internal configuration and avoid kinking during navigation to and from an interventional site and during operation at the interventional site. Infusion or withdrawal of liquids through the lumen of the tubular structure may be accomplished through a lumen provided by the catheter and, in this case, the structure of the catheter must have sufficient stiffness to resist both collapse and expansion of the lumen under a range of pressures and force conditions. Thus, it is essential that catheter structures used in connection with such devices be as flexible as possible during placement and removal yet have a high degree of structural integrity, permitting the catheter to be navigated and to serve as a conduit for fluids and internal structures during and/or following placement.

Many catheters have a composite construction that provides greater stiffness and support in certain areas, such as proximal areas, and more flexibility in other areas, such as distal areas. Variable stiffness along the length of a catheter is typically provided by varying the construction and/or diameter and/or wall thickness and/or material composition along the length of the catheter. There are many examples of catheters having variable stiffness along their lengths in the prior art literature. Some previous attempts at designing a kink-resistive tubular structure provided a layer of a coiled, braided or otherwise weaved member that has tight loops and that is fixedly attached to or embedded in a polymeric layer, such as a polyimide or plastic layer. Although the construction of the layer may allow for a small amount of flexibility, the use of a woven or coiled layer attached to or embedded in a polymeric layer generally results in a tubular structure that is stiffer in portions of the structure than which is required by many applications. Some tubular structure designs that include such layers are described in U.S. Pat. Nos. 6,464,684; 6,197,014; and 5,868,767. U.S. Patent Publication US-2004-0230212-A1 discloses a different type of catheter structure providing a lumen, an overlying layer and a coil element support layer that is attached to the overlying layer at a bonding point but otherwise slippable relative to the overlying layer. This slippable relationship between the coil element and an overlying layer improves flexibility and reduces kinking Many types of catheters include reinforcing structures, such as tubular structures, along at least an area of their length. Tubular members used in catheter construction may have a reduced diameter and/or a reduced wall thickness along at least an area of their length to provide increased flexibility, and may additionally be scored or cut to increase their flexibility. U.S. Pat. No. 4,960,410 discloses, for example, a relatively stiff tube that is spirally scored or cut along a portion of its length, such as the distal portion, to increase its flexibility. The spirally cut or scored tube is covered by a more flexible tube. U.S. Pat. No. 5,573,520 discloses a catheter structure in which a self-supporting tube having a plurality of apertures, such as spiral apertures or discontinuous slots, is encased by a covering to provide a catheter structure providing a lumen having a fluid-tight seal. U.S. Pat. No. 5,599,326 disclose a catheter section including an elongate tubular member comprising an inner stiffener liner of a spirally cut polymeric tubing member and an outer tubular cover comprising a polymeric cover material. U.S. Pat. No. 5,843,050 discloses diagnostic and/or therapeutic microcatheters that are highly flexible and may have a tubular wall with two coaxial tubular elements in the wall, each of the tubular elements provided with a spiral cut in its distal zone to increase flexibility.

U.S. Pat. No. 6,048,338 describes various types of catheters having an elongate shaft with a transition in flexibility and a transition tube disposed about the shaft and having a spiral cut, easing bending of the shaft. The transition tube may have only one end secured to the catheter shaft, and the pitch of the spiral cut may be varied. U.S. Pat. No. 6,254,588 discloses a catheter having a spiral cut tubular member within a flexible body having at least one flexibility gradient zone, with a different flexibility at a proximal end and at a distal end, and having a continuous change in flexibility between the two. Yet another patent, U.S. Pat. No. 6,652,508, proposes an intravascular catheter comprising a distal flexible tube having a spiral slot with coils disposed in the voids formed by the slots.

U.S. Patent Publication 2006/0100687 discloses a delivery catheter assembly having an inner metallic hypotube and an outer metallic hypotube, each of the hypotubes having spiral or circumferential slots interrupted at intervals by solid struts. The distal end of the tubes may have smaller pitch slots, and the proximal end of the tubes may have larger pitch slots to vary the flexibility along the length of the catheter. U.S. Patent Publication 2009/0062602 discloses a flexible spine for use in a catheter or a sheath. The flexible spine is composed of a unitary structure having a plurality of discrete sections, each of which has a distinguishing structural attribute that differentiates it from other sections, wherein the arrangement of sections varies flexibility. An aperture structure having an expanded or enlarged I-shape, or a double-ended vase shape is disclosed.

Notwithstanding the numerous disclosures relating to catheter structures and the numerous types of catheters and sheaths available, improvements in catheter flexibility, versatility, pushability and other properties are highly desirable. The present invention is thus directed to sheath assemblies having improved properties for use with interventional catheter systems and interventional catheter systems incorporating such sheath assemblies.

SUMMARY OF THE INVENTION

The present invention relates to sheath assemblies for use as elongated, flexible tubular members. The sheath assemblies incorporate slotted structures at one or more areas that provide desired degrees of flexibility and bendability over the length of the sheath assembly. Different patterns and types of slotted structures may be used to provide different flexibility and bendability properties at various locations over the length of the sheath assemblies, yet maintain desirable pushability and non-kinking properties of the sheath. Sheath assemblies of the present invention are suitable for use in many types of tubular structures and flexible tubing applications, and particularly in medical devices such as interventional catheter systems having aspiration and/or infusion systems.

In one embodiment, the sheath assembly comprises at least one inner tubular member having an arrangement of discontinuous slots along at least a portion of its length, with at least some of the slots having an enlarged aperture at at least one terminus of the slot. In some embodiments, the slots may penetrate the full thickness of the inner tubular member, providing the slots as openings through the inner tubular member, while in alternative embodiments, the slots may penetrate less than the full thickness of the inner tubular member, essentially providing slots as a scored construction. A flexible outer tubular member may be provided contacting and extending for at least a portion of the length of the inner tubular member.

The inner tubular member is generally constructed from a material that is substantially rigid, such as a metallic material, or a rigid or semi-rigid polymeric material, and it is generally provided as a generally thin-walled tube. A desired degree of flexibility and bendability of the substantially rigid inner tubular member is provided along at least a portion of its length as a result of its slotted structure. Exemplary materials for constructing the inner tubular member include steel and stainless steel hypotubes, such as 304SS hypotube, which may be hardened or otherwise treated to impart desirable properties. Slots and apertures may be provided by laser cutting or other techniques that are well known in the art. In one embodiment, multiple independent tubular sections may be arranged in proximity to one another in an end-to-end or spaced apart end-to-end arrangement to provide an inner tubular member. In another embodiment, multiple tubular sections may be joined to one another (e.g., by spot welding, bonding, adhesives or the like) to provide an integral inner tubular member composed of several sections.

The outer tubular member may overly the inner tubular member along all or a substantial portion of the length of the inner tubular member. The outer tubular member is generally constructed from a flexible material and, in some embodiments, the outer tubular member may be extruded or heat-shrunk over the inner tubular member. Exemplary materials for the outer tubular member include PEBAX®, polyester, polyimide, and the like. In one embodiment, the outer tubular member may be in the form of a continuous tubular structure. Alternatively, the outer tubular member may be slotted or apertured, generally in a pattern different from the slot and/or aperture pattern of the inner tubular member. The outer tubular member may be provided as an integral tubular member or it may comprise multiple tubular members arranged in abutting, spaced apart or overlapping configurations. The outer tubular member may have a variable inner diameter and/or outer diameter and/or thickness over its length. In some embodiments, the outer tubular layer is bonded to the inner tubular member along the length of the interface; in alternative embodiments, the inner and outer tubular members are bonded to one another at one or more discrete locations along the length of the sheath assembly.

Different slotted constructions of the inner tubular member provided at different locations along the length of the inner tubular member, as well as (optional) areas of continuous, unslotted tube, provide multiple areas of desired flexibility and bendability of the sheath assembly over its length. In general, slots may be provided in a circumferential and/or helical orientation. In some embodiments, the slots are discontinuous, meaning that an unslotted, or "solid" tubular section separates each of the termini of each slot from termini of neighboring slots. The arrangement of slots may be staggered, such that neighboring slots begin and terminate at different regions on the circumference of the inner tubular member.

Helical slots may extend continuously for more than one circumference (i.e., >360° around the inner tubular member, or they may extend for less than one circumference (i.e., <360°) around the inner tubular member. In some embodiments, helical slots extend for more than 180° and less than 360° around the inner tubular member and slot termini (or apertures) are separated from neighboring slot termini (or apertures) by an unslotted region corresponding to less than about ¼ the circumference of the inner tubular member (i.e., <) 90°. In some embodiments, helical slots extend for a length of from about 180° to 300° around the inner tubular member and are separated from neighboring slots by an unslotted tubular section having a length corresponding to about 20° to about 60° around the inner tubular member. In some embodiments, helical slots extend for a length of from about 180° to about 260° around the inner tubular member and are separated from neighboring slots by an unslotted tubular section having a length corresponding to about 30° to about 50° around the inner tubular section. Helical slots extending for a length of about 230° separated by an unslotted region of about 40° are preferred for some applications.

Various sections of an inner tubular member may have different slot lengths and patterns, and slotted sections of an inner tubular member having different slot characteristics and patterns may neighbor one another, or may be separated from one another by continuous, unslotted sections of tubing. The slot length and pattern within a slotted section may also vary along the length of a section. In one embodiment, for example, the slot lengths in a slotted section may transition from a length of about 180° to a length of 230°, or more, over the length of the section. The dimensions of the unslotted tubular section located between neighboring slot termini may also vary over the length of a slotted section.

In some embodiments, an enlarged aperture is provided at one or both termini of one or more of the slots. The width of the enlarged aperture is generally at least twice the kerf width of the corresponding slot, and may be at least 3 times, or four times, or 10 times, or between 2 and 20 times the kerf width of the corresponding slot. The configuration of enlarged apertures may be generally circular, oval, oblong, triangular, or another shape. Different configurations for enlarged apertures may be used for different slot configurations along an inner tubular member and at different portions of the inner tubular member. In some embodiments, a major dimension of the enlarged aperture is oriented substantially orthogonal to the direction of the slot.

The enlarged apertures may provide significant stress relief during bending and flexing of the inner tubular member and the sheath assembly. Enlarged apertures may also substantially prevent fatigue and/or fatigue failure resulting from oscillations that may occur during the operation of an interventional catheter or another interventional device incorporating an inner sheath. Thus, in one aspect, the present invention is directed to methods for reducing, or substantially preventing fatigue and/or fatigue failure, and methods for providing stress relief along a sheath assembly. The methods involve providing a sheath assembly having an arrangement of discontinuous slots along at least a portion of its length, with at least some of the slots terminating in an enlarged aperture at at least one terminus of the slot(s). Any of the sheath embodiments disclosed herein may be used in these methods.

Those having ordinary skill in the art will appreciate that the dimensions of various components and features will vary significantly, depending on the diameter, thickness, material and construction of the inner tubular member, the application for which the sheath assembly is designed, the interventional catheter (or other medical device) in which the sheath assembly is incorporated, and the like. In general, slot kerf widths from about 0.2 to 5 times the thickness of the inner tubular member are suitable; slot pitches of from about 1 mm to about 10 mm are suitable for medical catheter and tubing applications; slot lengths from 0.3-10× the tubular circumference are generally suitable; and the distance between neighboring slots of from about 5× to about 100× the kerf width, or more, are suitable. In some embodiments, the pitch of slots may vary from about 0.2-2 mm; the slot kerf width may vary from 0.015-0.035 mm; and the enlarged aperture diameter may range from about 5-10× kerf width.

The kerf width of the slots may be different in different regions of the inner tubular member. The pitch of helical slots may be different in different regions of the inner tubular member and is generally smaller at distal regions of the inner tubular member and larger at more proximal regions of the inner tubular member. The space between slots, or frequency of slots, may be different in different regions of the inner tubular member and is generally smaller at distal regions of the inner tubular member.

Numerous regions of the inner tubular member may be defined by different slot patterns, different slot sizes and kerf widths, different slot pitches, different slot frequencies, the presence or absence of slots, the presence or absence of enlarged apertures at one or both termini of at least one slot, enlarged aperture dimensions relative to slot dimensions, enlarged aperture configurations, and the like. Within each section, the slot properties may be uniform for the section, or the slot properties may vary along the length of the section. Some regions of the inner tubular member may be unslotted and substantially solid. In some embodiments, for example, slotted sections having different slot patterns and characteristics may be interspersed with non-slotted sections having a substantially continuous surface area. Tubular members having different inner and/or outer diameter dimensions, different thicknesses, different materials, and the like, may be arranged in proximity to one another and/or joined to one another to form an elongated inner tubular member.

In some embodiments, the pitch of slots generally decreases toward the distal end of the inner tubular member. In another embodiment, the pitch of slots decreases toward the distal end for a portion of the length of the inner tubular member, and a section in proximity to the distal end of the tubular member has slots with a larger pitch.

In some embodiments, the inner tubular member comprises a single continuous tube, which may have a constant diameter or variable diameter along its length. The diameter of the inner tubular member may decrease along its length, for example, with a larger diameter portion provided in a proximal region and a smaller diameter portion provided in a distal region. The change in diameter along the length of the inner tubular member may be constant along the length or variable along the length of the tubular member. In alternative embodiments, the inner tubular member may be provided as two or more tubular members joined together or mounted in the sheath assembly in proximity to one another. Multiple tubular members forming an inner tubular member may have different diameters, structures, and the like, and may be composed of different materials. In one embodiment, the inner tubular member comprises at least two substantially rigid tubes having different inner diameters and/or outer diameters joined to one another, with at least one of the tubes having an arrangement of discontinuous slots along at least a portion of its length.

While the slots are generally provided to increase the flexibility of the inner tubular member and many embodiments provide increased flexibility along the length of the tubular member in the distal direction, increased flexibility in a distal direction isn't necessary or required for all applications. In some embodiments, the slots and slot configurations provide regions of greater and/or less flexibility/bendability along the length of the inner tubular member and, consequently, along the length of the sheath assembly and catheter system.

Catheter systems of the present invention may include additional tubular members forming additional sheath layers and/or may form one or more lumens using additional tubular members having different inner and outer diameters. In general, catheter systems of the present invention comprise a sheath assembly having an inner tubular member having discontinuous slots over at least a portion of its length and having apertures at least at one termini of at least some of the slots contacting a flexible outer layer over a substantial portion of its length, and an operating head positioned at a distal end of the sheath assembly. The operating head may be connected directly, or indirectly, to the sheath assembly. An operating head, such as a rotatable operating head, for example, may be mounted to a drive shaft that rotates independently of and traverses the sheath assembly coaxially. Alternatively, an operating head, or an operating head component, may be connected to the sheath assembly directly, or indirectly, through one or more bearings or intermediate components.

The sheath assembly may extend for substantially the full length of an interventional catheter, or for only a part of it. A proximal end of the sheath assembly, or the interventional catheter, may be associated with, such as mounted to, a control component of the interventional catheter assembly. Exemplary interventional catheters and control components are well known in the art.

BRIEF DESCRIPTION OF THE DRAWINGS

FIG. 3A shows an enlarged schematic image illustrating a portion of an inner tubular member having helical slots with an enlarged aperture provided at each terminus of each helical slot.

FIG. 3B shows an enlarged schematic image illustrating a portion of an inner tubular member similar to that shown in FIG. 3A but having higher frequency and smaller pitch slots compared to the frequency and pitch of slots illustrated in the section shown in FIG. 3A.

FIG. 5 shows an enlarged schematic view of one embodiment of a sheath assembly of the present invention illustrating at least two inner tubular members joined to provide a composite inner tubular member with a flexible overlying layer.

FIG. 6 shows an enlarged schematic view of an example catheter system.

Like numbers have been used to designate like parts throughout the drawings to provide a clear understanding of the relationship of the various components and features, even though different embodiments are illustrated. It will be understood that the appended drawings are not necessarily to scale, and that they present a simplified, schematic view of many aspects of systems and components of the present invention. Specific design features, including dimensions, orientations, locations and configurations of various illustrated components may be modified, for example, for use in various intended applications and environments.

DETAILED DESCRIPTION

Figure 1:
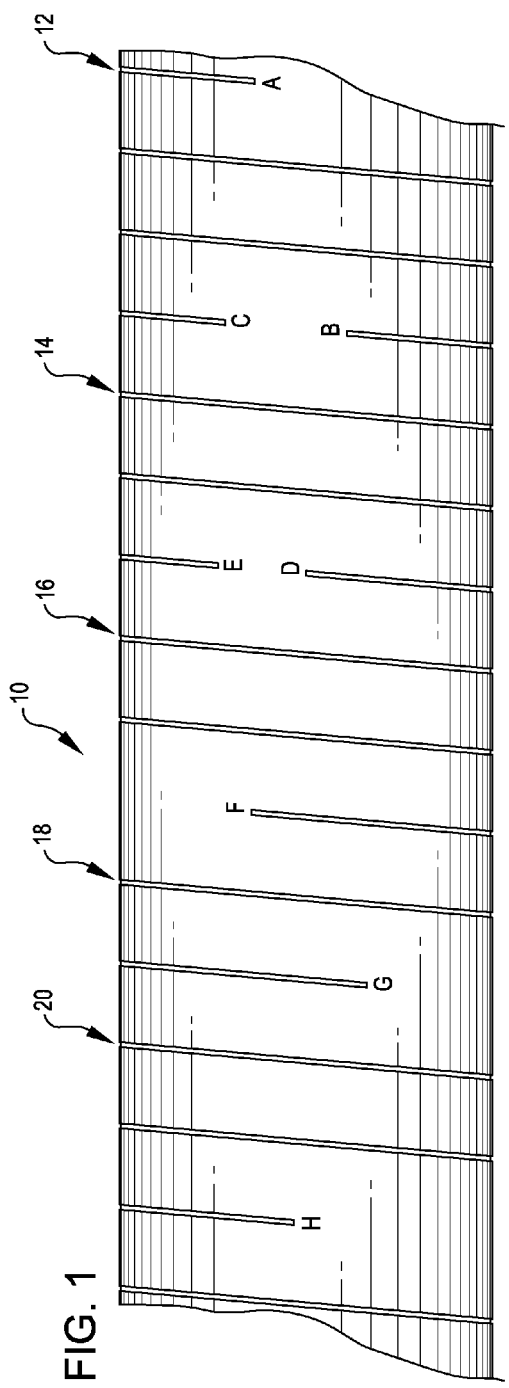
FIG. 1 shows an enlarged schematic image illustrating a portion of an inner tubular member having the termini of helical slots arranged in a staggered pattern.

FIG. 1 shows an image illustrating one embodiment of a portion of an inner tubular member having a plurality of slots. Inner tubular member 10 may be formed as a length of 304 stainless steel hypotube, for example, having slots laser cut through the hypotube. The slots illustrated in this embodiment are provided in a spiral configuration, and each slot extends for greater than one circumference of the tubular member. Slot 12 has one terminus at A and another at B; slot 14 has one terminus at C and another at D; slot 16 has one terminus at E and another at F; slot 18 has one terminus on a "reverse" surface area of member 10 (not shown) and another at G; slot 20 has one terminus on a "back" surface area of member 10 (not shown) and another at H. Each of the slots extends in a spiral configuration and has a length greater than that of the circumference of tubular member 10.

The slots have different lengths, and the termini of neighboring slots are staggered with respect to the circumference of the tubular member. In the embodiment shown in FIG. 1, the slot termini (e.g., A, B, C, D, E, F, G) are staggered along the length of the tubular member. The distance between the termini of neighboring slots may vary, as shown. It will be appreciated that different slot patterns and stagger patterns may be implemented.

The slots shown in FIG. 1 penetrate the tubular wall and have a substantially uniform kerf (slot) width along their lengths. Each of the slots has generally the same width, and the slots do not have enlarged apertures at their termini. It will be appreciated that slots having graduated kerf widths along their length may be provided, and that neighboring slots having different kerf widths may be provided. In the embodiment illustrated in FIG. 1, each of the slots has substantially the same pitch; in alternative embodiments, slots having different pitches, or sections of slots having different pitches, may be provided.

Figure 2:
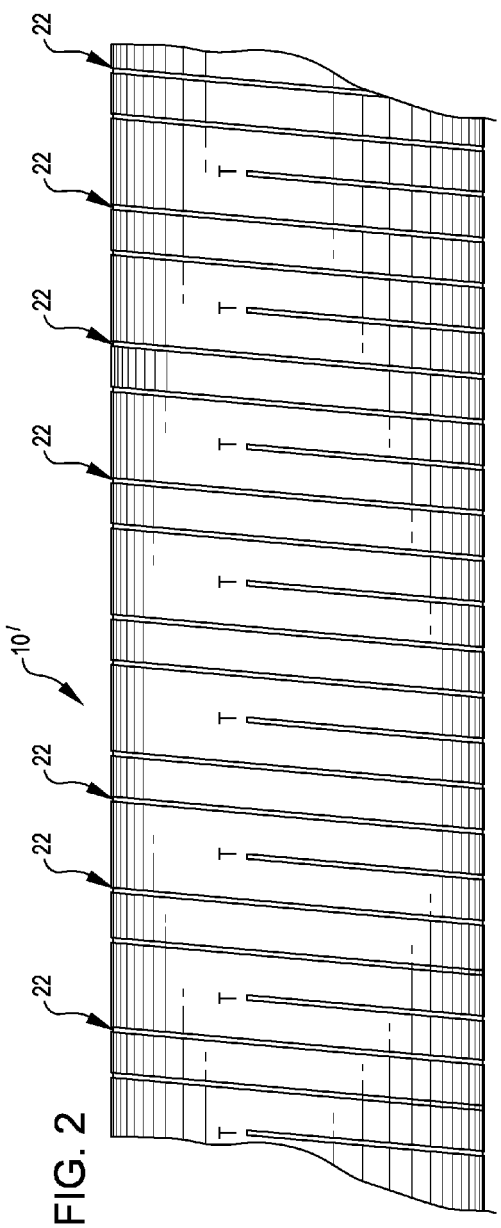
FIG. 2 shows an enlarged schematic image illustrating a portion of an inner tubular member having higher frequency and smaller pitch slots compared to the frequency and pitch of slots illustrated in the section shown in FIG. 1, and having the termini of helical slots arranged in a linear pattern.

FIG. 2 shows an image illustrating another embodiment of a portion of an inner tubular member 10' having a plurality of slots 22. Slots 22 illustrated in this embodiment are provided in a spiral configuration and have a higher frequency, or a smaller dimension between slots, than the slots provided in inner tubular member 10 illustrated in FIG. 1. In this embodiment, each of the slots 22 has generally the same length, with one terminus of each slot located on the visible portion of the tubular member and another terminus (not shown) on the reverse surface of tubular member 10'. In this embodiment, at least one terminus T of each neighboring slot is located in essentially the same position with respect to the circumference of the tubular member. Slots 22 shown in FIG. 2 have a substantially uniform kerf width along their lengths, each of the slots has generally the same kerf width, and the slots do not have enlarged apertures at their termini. It will be appreciated that slots having different kerf widths along their length, and neighboring slots having different kerf widths, and enlarged apertures at the termini of and/or along the length of one or more slots may be provided.

Figure 3C:
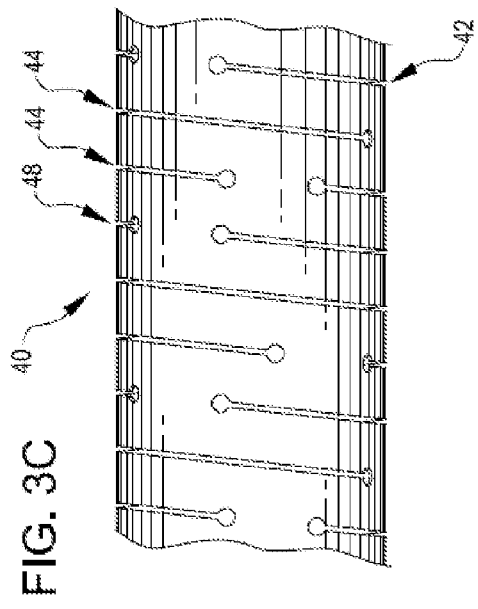
FIG. 3C shows an enlarged schematic image illustrating a portion of an inner tubular member similar to those illustrated in FIGS. 3A and 3B but having different slot configurations and a staggered arrangement of enlarged apertures.

FIGS. 3A-3C illustrate exemplary portions of inner tubular members of the present invention incorporating slots with enlarged apertures provided at at least one termini of each of the slots. The apertures are shown as generally circular, having a diameter at least 2× the kerf width of the corresponding slot and, more generally, at least 3× the kerf width of the corresponding slot. For example, as shown in FIG. 3A the slot may have a kerf width $W_1$, and the enlarged aperture may have a width $W_2$. Further, the width of the enlarged aperture is generally at least twice the kerf width of the corresponding slot, and may be at least 3 times, or four times, or 10 times, or between 2 and 20 times the kerf width of the corresponding slot. Enlarged apertures are generally centered with respect to the longitudinal axis of the slots; in alternative embodiments, enlarged apertures may be provided in an off-center relationship to the longitudinal axis of the slots. The length, frequency, pitch, kerf width and pattern of slots, and the size, location and pattern of enlarged apertures may vary.

FIG. 3A shows a section of a tubular member 30 in which a plurality of slots 32, 34, 36, 38 are provided. Each of the slots 32, 34, 36, 38 has a length in excess of twice the circumference of tubular member 30, and each of the slots terminates, at each terminus, in an enlarged aperture A. In the embodiment illustrated in FIG. 3A, the distance between apertures (A) of neighboring slots is less than the circumference of tubular member 30, and is generally less than about 90° and often less than about 60°. Apertures (A) at the termini of neighboring slots are arranged in a regular pattern along the length (or along the length of any particular section) in the embodiment illustrated in FIG. 3A.

FIG. 3B shows a section of a tubular member 30' in which a plurality of slots 32', 34', 36', 38' are provided. Slots 32', 34', 36', 38' illustrated in this embodiment are provided in a spiral configuration and have a higher frequency, or a smaller dimension between slots, than the slots provided in inner tubular member 30 illustrated in FIG. 3A. Each of the slots 32', 34', 36', 38' has a length in excess of twice the circumference of tubular member 30, and each of the slots terminates, at each terminus, in an enlarged aperture A. In the embodiment illustrated in FIG. 3A, the distance between apertures (A) of neighboring slots is less than the circumference of tubular member 30, and is generally less than about 60°. Apertures (A) at the termini of neighboring slots are arranged in a regular pattern along the length (or along the length of any particular section) in the embodiment illustrated in FIG. 3B.

FIG. 3C illustrates a section of tubular member 40 having a plurality of helical slots, e.g., 42, 44, 46, 48. The length of each of the slots is less than the circumference of tubular member 40, generally extending from about 220° to about 350° around the circumference of tubular member 40 and, in some embodiments, from about 270° to about 340°. An enlarged aperture is located at each terminus of each slot, and the distance between the termini of neighboring slots is from about 10° to about 140°, generally from about 20° to about 90°. The slot positioning is irregular, at least over a short repeat of 4-5 slots, and the apertures are staggered, at least over a short repeat of 4-5 slots, as shown.

Figure 4:
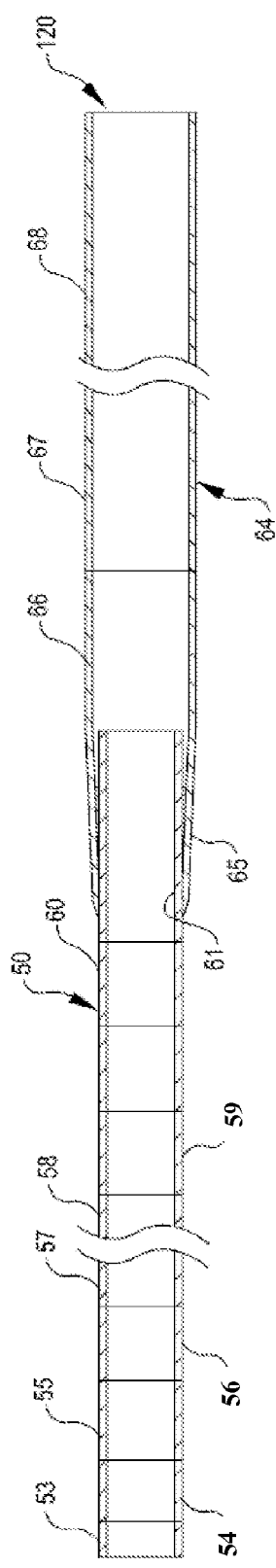
FIG. 4 shows an enlarged schematic view of one embodiment of a sheath assembly of the present invention.

The exemplary tubular members illustrated above, having different slot and aperture arrangements, may represent relatively short, or longer, sections of a tubular member. Different slotted constructions and arrangements, with or without apertures, provided at different locations along the length of an inner tubular member, as well as (optional) areas of continuous, unslotted tube, provide areas of desired flexibility and bendability of the sheath assembly over its length. In one embodiment, illustrated schematically in FIG. 4, tubular body 50 comprises a smaller diameter section 52 and a larger diameter section 64. Smaller diameter section 52 comprises a plurality of sections 53, 54, 55, 56, 57, 58, 59, 60 and 61, and may form one layer of the distal portion of a catheter or catheter-based device. Each section comprises a portion of the tubular member having different slot characteristics. Some sections, such as distal section 53 and proximal section 61, may be unslotted and form attachment areas for other tubular members, components, or the like. Other sections may have different slot constructions (e.g., slot lengths, pitches, kerf widths, apertures, aperture sizes, and the like).

In one exemplary embodiment, for example, tubular section 54 slotted, with the slots having a helical configuration and having a constant pitch of about 0.2 mm along the length of section 54. The slot length varies over the length of section 54 and transitions in a graduated (e.g., linear) fashion from a length of 180° (around the circumference of the tubular member) to a length of about 230°. Each slot has a circular aperture at each of its termini, and the space between apertures forming the termini of neighboring slots is variable and transitions in a graduated (e.g., linear) fashion over the length of section 54 from a length of 90° (around the circumference of the tubular member) to a length of 40°. In this exemplary embodiment, neighboring section 55 is also slotted and has a constant pitch of about 0.2 mm. Each of the slots in section 55 has a constant length of about 230°, with circular apertures at each slot termini. The space between apertures forming the termini of neighboring slots in section 54 is constant and is about 40°.

Tubular sections 56, 57, 58 and 59, in this exemplary embodiment, are slotted and have the same or similar slot lengths. The kerf width may be substantially the same, or may be different in different sections. In one embodiment, the slots provided in tubular sections 56-59 do not have apertures; in other embodiments, all or some of the slots in each section may have apertures at their termini. In one embodiment, the pitch of slots in section 56 is constant and is substantially the same as the pitch of neighboring section 55 (e.g., about 0.2 mm). The pitch of slots in neighboring section 57 increase over the length of section 57, for example, in a linearly graduated fashion, with the pitch of slots varying from about 0.2 mm to about 0.25 mm over the length of section 57. Neighboring section 58 may also be slotted, with the pitch of the slots constant and about 0.25 mm. Neighboring section 59 may also be slotted, with the pitch of slots in section 59 increasing over the length of the section, for example, in a linearly graduated fashion, with the pitch of the slots varying from about 0.25 mm to about 0.4 mm. Tubular section 60 may also be slotted, with the pitch of the slots being further graduated, in a linear or non-linear fashion, between a pitch of from about 0.4 to 0.8 mm. In one embodiment, slots in tubular section 60 may be provided with apertures at their termini. Tubular section 61 may be provided as a non-slotted section that overlaps with, or underlays, larger diameter tubular section 64 and is bonded to section 64.

The kerf width of slots in different sections of smaller diameter tubular section 50 may be constant, or may vary. In general, the kerf width of slots is smaller toward a distal end of tubular section 50 and larger toward a proximal end of tubular section 50. Similarly, the kerf width of slots within a single section may be constant or may vary. The diameter of apertures provided at slot termini may likewise vary in different tubular sections and with different kerf widths, slot lengths, and the like. In general, the diameter, or largest dimension of the apertures provided at slot termini is from about 2× to about 10× the kerf width. In many embodiments, the diameter, or largest dimension of the apertures provided at slot termini is about 3× to about 7× the kerf width of the corresponding slot.

Larger diameter tubular section 64 may also comprise multiple sections having different slot properties, and having both slotted sections and non-slotted sections. In one embodiment, for example, larger diameter tubular section 65 is unslotted and overlaps and is bonded to smaller diameter tubular section 50. Neighboring tubular section 66 may be slotted, with slots having a length of less than 230° (e.g., from about 150° to about 230°) and a distance between slot termini of from about 20° to about 90° (e.g., about 40°). In one embodiment, the slots of tubular section 66 have a graduated (e.g., linearly graduated) pitch of from about 0.4 to 1 mm.

Tubular section 67 may be slotted or unslotted. In one exemplary embodiment, slots in section 67 have generally the same lengths as those of neighboring section 66, and have a substantially constant pitch of 1 mm, for example. Tubular section 68 may be slotted or unslotted. In one exemplary embodiment, slots in section 68 have a gradual pitch (e.g., linearly graduated) of from about 1 to 2 mm. More proximal tubular sections may be slotted or unslotted and, if slotted, may have a larger pitch.

FIG. 5 schematically illustrates a sheath assembly 100 of the present invention having a smaller diameter distal end 110 and a larger diameter proximal end 120. The sheath assembly incorporates an inner tubular member 104 and an outer tubular member 106. In the embodiment illustrated in FIG. 5, inner tubular member 104 is provided as a composite assembly formed by joining a smaller diameter distal portion 102 to a larger diameter proximal portion 108 at junction 105. Outer tubular member 106 may be extruded or heatshrunk over the composite inner tubular member.

Sheath assemblies of the present invention may be incorporated in various types of catheter assemblies and in other types of medical tubing and devices. Additional tubular layers may be provided overlying and/or underlying the sheath assembly and may be substantially contacting an outer and/or inner layer of the sheath assembly, or may be provided to form lumens using an outer and/or inner layer of the sheath assembly. Functional components such as guidewires, drive trains, etc. may be incorporated in catheter assemblies and other types of medical devices.

Simple interventional catheter systems may provide aspiration and/or infusion functions, providing fluids to a desired interventional site using an infusion system and/or removing fluid and debris from an interventional site using an aspiration system. More complex interventional catheter systems, such as catheter system 200 shown in FIG. 6, may incorporate an operating head 210 provided in proximity to a distal end of the interventional catheter 212 and communicating with a material removal or ablation operating system 214 located in an intermediate housing assembly or in a control console 216. Further, a proximal end of the sheath assembly, or the interventional catheter, may be associated with, such as mounted to, a control component of the interventional catheter assembly. Interventional catheters are sized and configured for insertion into a patient and typically comprises an elongated, flexible catheter and an operating head positioned in proximity to a distal end of the catheter and mounted on the catheter and/or on a drive system that transits the catheter. Interventional catheter may also incorporate aspiration and/or infusion lumens or channels providing fluidic communication between a distal end of the interventional catheter positioned as a site of intervention and externally positioned aspiration and/or infusion components of the interventional catheter.

We claim:

1. A medical device comprising:
   a sheath assembly including a lumen and an inner tubular member having a plurality of discontinuous slots along at least a portion of its length, wherein the plurality of slots includes a first slot having an enlarged aperture at a terminus and a flexible outer tubular member contacting and extending for at least a portion of the length of the inner tubular member;
   a rotatable drive shaft disposed along the lumen, wherein the drive shaft includes a distal end region and a proximal end region;
   a rotatable operating head coupled to the distal end region of the drive shaft; and
   a control console coupled to the proximal end region of the drive shaft.

2. The medical device of claim 1, wherein the inner tubular member has a plurality of sections having different arrangements of discontinuous slots along the length of at least two sections.

3. The medical device of claim 2, wherein the inner tubular member has a plurality of sections having different lengths of discontinuous slots along the length of at least two sections.

4. The medical device of claim 3, wherein at least one of the sections has slots having different slot lengths neighboring one another.

5. The medical device of claim 2, wherein at least one of the sections has slots with slot lengths that vary over the length of the section, the slot lengths transitioning in a graduated fashion from a shorter length to a longer length.

6. The medical device of claim 2, wherein the inner tubular member has a plurality of sections having different patterns of discontinuous slots along the length of at least two sections.

7. The medical device of claim 1, wherein the first slot has a second aperture at a second terminus.

8. The medical device of claim 1, wherein the first slot has a slot width and the enlarged aperture has an aperture width, and wherein the aperture width is at least twice the slot width.

9. The medical device of claim 1, wherein the first slot has a slot width and the enlarged aperture has an aperture width, and wherein the aperture width is at least 4 times the slot width.

10. The medical device of claim 1, wherein the at least some discontinuous slots extend for a length greater than the circumference of the inner tubular member.

11. The medical device of claim 1, wherein the at least some discontinuous slots extend for a length greater than 360° around the circumference of the inner tubular member.

12. The medical device of claim 1, wherein the at least some discontinuous slots extend for a length greater than 180° around the circumference of the inner tubular member and less than the circumference of the inner tubular member.

13. The medical device of claim 1, wherein slot termini, or enlarged apertures provided at slot termini, are separated from neighboring slot termini or enlarged apertures by unslotted regions extending for a length of less than 90° around the circumference of the inner tubular member.

14. The medical device of claim 1, wherein the inner tubular member comprises at least two tubular sections arranged end-to-end and joined to one another.

15. The medical device of claim 14, wherein the tubular sections have different diameters.

16. A catheter system comprising the medical device of claim 1, wherein the operating head is connected, directly or indirectly, at a distal end of the sheath assembly.

17. A catheter system of claim 16, wherein the operating head rotates independently of and traverses the sheath assembly coaxially.

18. A catheter system of claim 16, additionally comprising a control component associated with the control console.

* * * * *